· US008289284B2

(12) United States Patent
Glynn et al.

(10) Patent No.: US 8,289,284 B2
(45) Date of Patent: Oct. 16, 2012

(54) CONTROLLER USER INTERFACE FOR A CATHETER LAB INTRAVASCULAR ULTRASOUND SYSTEM

(75) Inventors: Timothy Glynn, Centereach, NY (US); Nancy Perry Pool, El Dorado Hills, CA (US); Ed Oliver, Folsom, CA (US); Duane De Jong, Elk Grove, CA (US)

(73) Assignee: Volcano Corporation, San Diego, CA (US)

( * ) Notice: Subject to any disclaimer, the term of this patent is extended or adjusted under 35 U.S.C. 154(b) by 668 days.

(21) Appl. No.: 12/188,674

(22) Filed: Aug. 8, 2008

(65) Prior Publication Data

US 2009/0195514 A1    Aug. 6, 2009

Related U.S. Application Data

(60) Provisional application No. 60/954,965, filed on Aug. 9, 2007.

(51) Int. Cl.
   *G06F 3/041* (2006.01)
(52) U.S. Cl. ........................................ 345/173; 600/437
(58) Field of Classification Search .......... 345/173–178, 345/905; 178/18.01–18.11; 600/437–461
   See application file for complete search history.

(56) References Cited

U.S. PATENT DOCUMENTS

| | | | |
|---|---|---|---|
| 5,765,565 A * | 6/1998 | Adair .......................... | 128/849 |
| 5,805,144 A * | 9/1998 | Scholder et al. ............. | 345/163 |
| 6,358,207 B1 | 3/2002 | Lathbury et al. | |
| 6,540,685 B1 | 4/2003 | Rhoads et al. | |
| 6,709,397 B2 | 3/2004 | Taylor | |
| 6,821,250 B2 | 11/2004 | Mesaros et al. | |
| 7,594,847 B1 * | 9/2009 | York et al. ..................... | 463/5 |
| 2004/0015079 A1 | 1/2004 | Berger et al. | |
| 2004/0116908 A1 | 6/2004 | Birkenbach et al. | |
| 2007/0016028 A1 * | 1/2007 | Donaldson et al. ............ | 600/437 |
| 2007/0016029 A1 * | 1/2007 | Donaldson et al. ............ | 600/437 |
| 2007/0043597 A1 * | 2/2007 | Donaldson ..................... | 705/3 |
| 2007/0225590 A1 * | 9/2007 | Ramos ........................... | 600/407 |
| 2007/0232933 A1 * | 10/2007 | Gille et al. .................... | 600/481 |
| 2007/0252068 A1 * | 11/2007 | Secora ........................... | 248/458 |
| 2008/0112842 A1 * | 5/2008 | Edwards ........................ | 422/2 |

OTHER PUBLICATIONS

Sportstek, Club Portable Ultrasound Machine, Aug. 27, 2006.*
International Search Report and Written Opinion for PCT/US2008/72619 dated Nov. 5, 2008.

* cited by examiner

*Primary Examiner* — Amare Mengistu
*Assistant Examiner* — Dmitriy Bolotin
(74) *Attorney, Agent, or Firm* — Haynes and Boone, LLP

(57) ABSTRACT

A touchpad controller for a componentized intravascular ultrasound system is disclosed for acquisition and display of intravascular information in a catheter lab environment. The system includes a patient interface module (PIM) adapted to hold a catheter having an imaging probe located near a distal end, a control panel, a monitor for displaying images and patient data, and a processing unit. The touchpad controller facilitates use beneath a sterile drape and sensitivity to gloved touch. Furthermore, the touchpad controller is sized for handheld use during an imaging session. A rail mount facilitates easy attachment of the touchpad controller alongside a patient table.

24 Claims, 12 Drawing Sheets

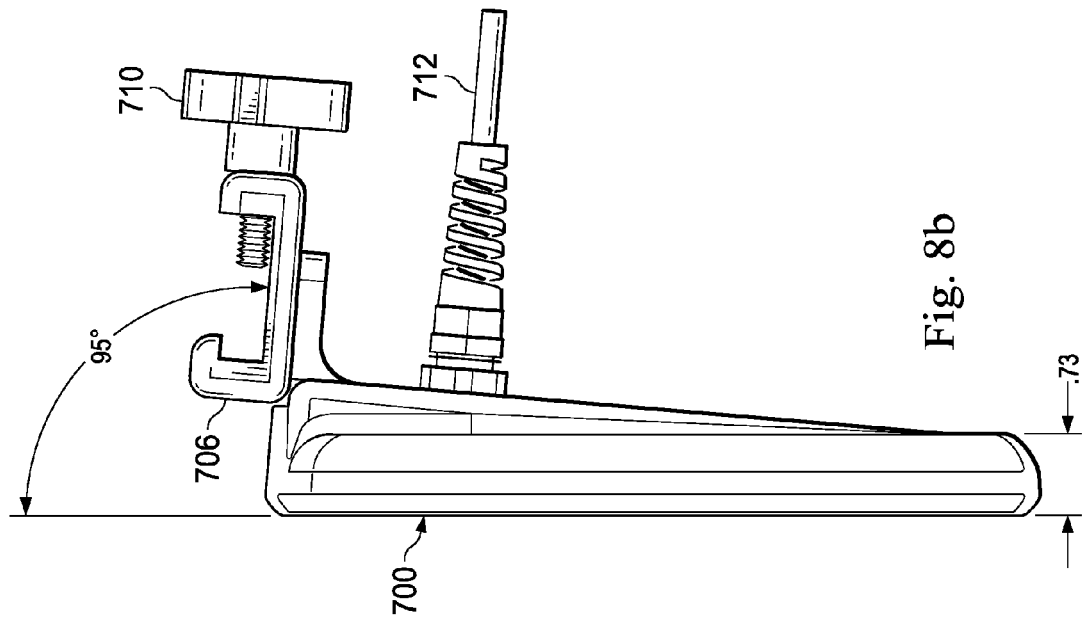
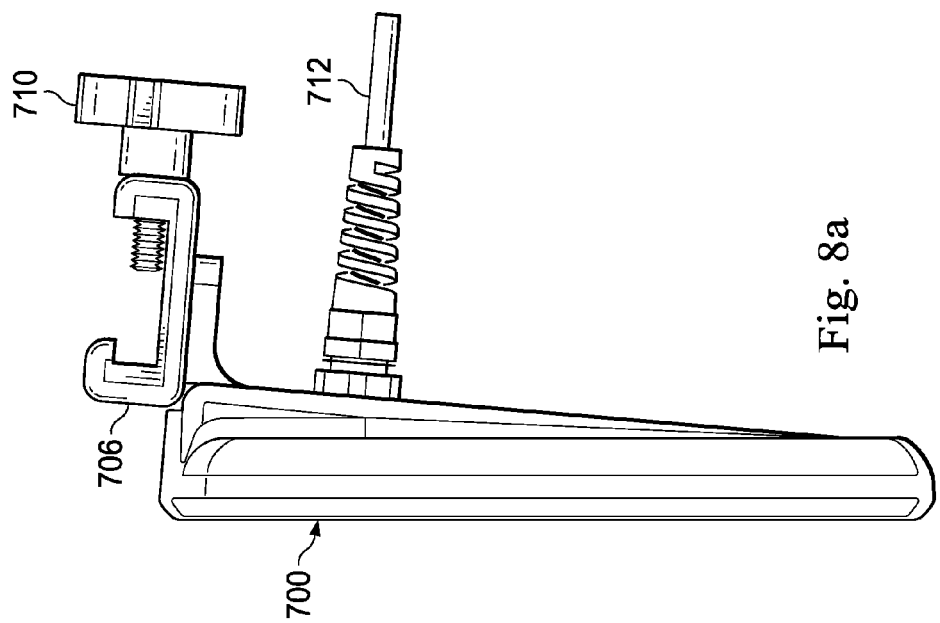

CONTROLLER USER INTERFACE FOR A CATHETER LAB INTRAVASCULAR ULTRASOUND SYSTEM

CROSS-REFERENCE TO RELATED APPLICATIONS

This application claims the priority benefit of Glynn et al, U.S. Provisional Patent Application Ser. No. 60/954,965, filed on Aug. 9, 2007, which relates to Pool et al. U.S. provisional application Ser. No. 60/825,813 filed on Sep. 15, 2006, entitled "Control Panel for a Catheter Lab Intravascular Ultrasound System", and Gille et al. U.S. application Ser. No. 11/549,402 filed on Oct. 13, 2006, entitled "Component-Based Catheter Lab Intravascular Ultrasound System." The contents of all of the above-identified applications are expressly incorporated herein by reference in their entirety including the contents and teachings of any references contained therein.

FIELD OF THE INVENTION

The present invention generally relates to the field of ultrasound imaging systems, and more particularly to systems used to diagnose and treat vascular disease.

BACKGROUND OF THE INVENTION

The development of new medical technologies has provided an increasing number of options available to doctors for the diagnosis and treatment of cardiovascular diseases. The availability of such equipment has improved the ability of doctors and surgeons to detect and treat cardiovascular disease. Intravascular imaging technologies have enabled doctors to create and view a variety of images generated by a sensor inserter within a vasculature. Such images compliment traditional radiological imaging techniques such as angiography by providing images of the tissue within vessel walls rather than showing a two dimensional lumen image.

In the area of cardiovascular imaging, doctors now routinely rely upon a variety of products and technologies including intravascular ultrasound (IVUS), angiogram, and MRI imaging devices. In fact, a recent trend is to combine external and invasive (IVUS) imaging methods within a single session with a patient. In fact such diverse technologies are now used even simultaneously to improve tracking the progress of a diagnostic and/or treatment device mounted upon a catheter during treatment of a patient.

Known IVUS systems such as the InVision system from Volcano Corporation are relatively large multi-component systems that are mounted upon a trolley that takes up a space about the size of a small refrigerator. These systems contain the displays, control panels, power supplies and computers in a single large chassis that is mounted upon a set of wheels to facilitate easy movement to any operating room/imaging lab where it is needed.

A potential barrier to adoption of invasive imaging techniques is the ease of use of such systems. Known systems tend to include generalized interfaces that are not particularly suited/adapted for use in a catheter lab where space is limited and ease of use is desired when a procedure must be completed potentially very quickly and without error. Training is a problem due to staff turn over, so a system that is easy to learn how to use and retain the information is very important.

SUMMARY OF THE INVENTION

In accordance with the present invention a controller user interface for an intravascular ultrasound (IVUS) system is described herein. The system includes a control panel through which a user controls the acquisition and display of IVUS image information. In illustrative embodiments the physical interface of the control panel is divided into regions associated with particular workflow functionality. The combination of a touchpad cursor control and functional regions and functions performed by controls (e.g., buttons/keys, touchpad, etc.) within particular regions facilitates a superior user experience including an enhanced learning curve as well as an ability to make selections by feel (as opposed to sight). In the disclosed embodiment a first region includes a set of IVUS action buttons, a second region includes a touchpad pointer navigation control with multi-button mouse functionality, and a third region includes controls for selecting modes of IVUS operation.

Furthermore, the touchpad control panel is mountable on a patient table rail or alternatively held in the hands of a user while operating the IVUS system. The touchpad interface includes raised rims around the buttons/regions to aid positioning of finger tips while operating the control panel. The touchpad control panel is sized sufficiently large to facilitate easy positioning of hands, yet small enough to hold in one's hand while controlling the operation of the system.

BRIEF DESCRIPTION OF THE DRAWINGS

While the claims set forth the features of the present invention with particularity, the invention, together with its objects and advantages, may be best understood from the following detailed description taken in conjunction with the accompanying drawing of which:

FIGS. 8a and 8b depict a side view of the touchpad control panel including a view of an exemplary mounting bracket for mounting to a rail.

DETAILED DESCRIPTION OF THE DRAWINGS

The IVUS (intravascular ultrasound) system including a touchpad controller embodying the present invention is based on the functionality derived from existing IVUS systems, including the CHROMAFLO flow imaging feature and other features present in the existing system. An exemplary system uses legacy internal circuit board architectures incorporated into previously provided systems, including, for example, analog and digital boards. The components of an exemplary system and their general descriptions are provided herein below with reference to FIG. 1. The components are physically divided, appropriately sized, and connected in a manner that improves their ability to seamlessly integrate with existing catheter lab/operating room infrastructure and thereby maximize accessibility to a patient and other medical equipment in the room.

Figure 1:
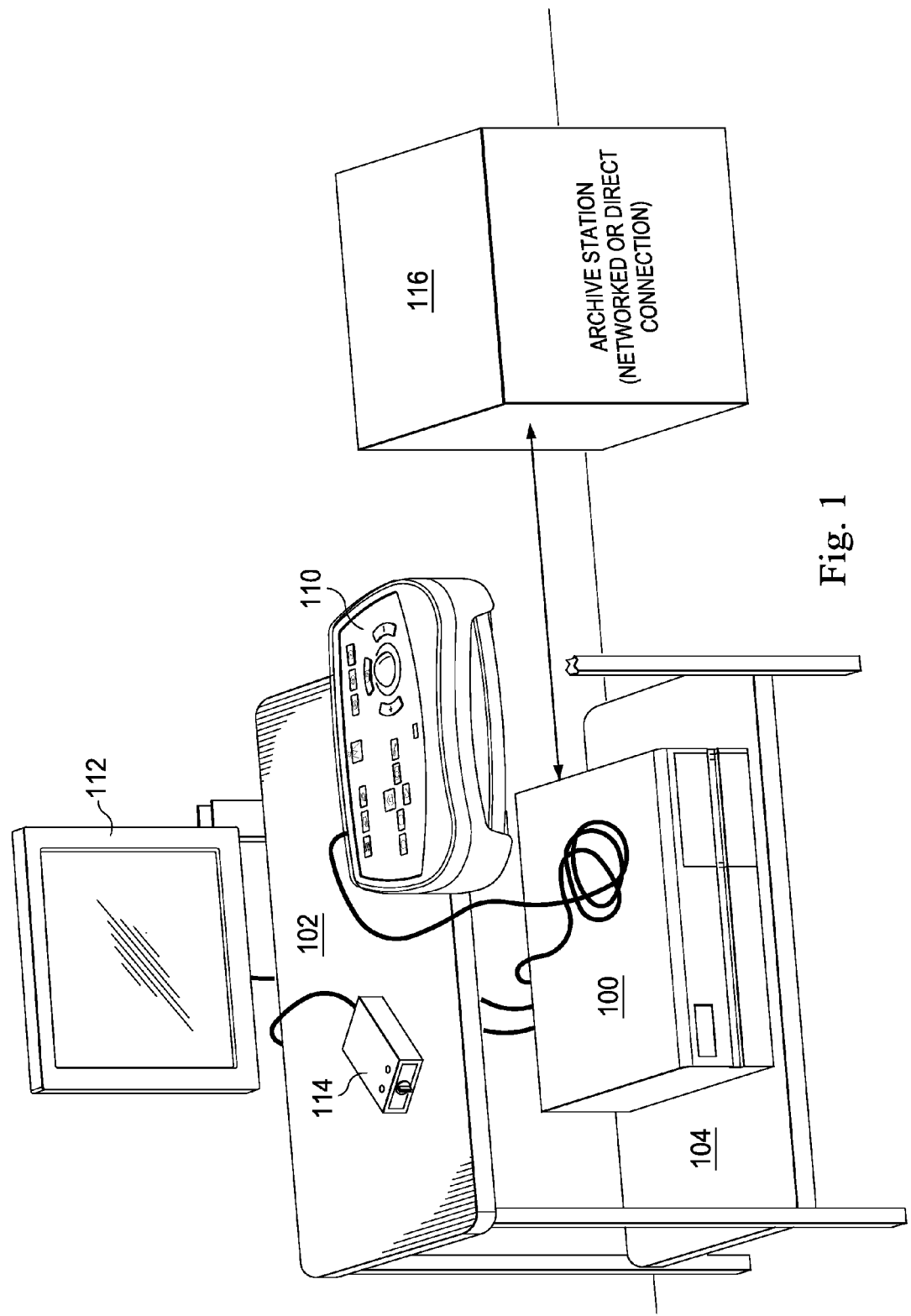
FIG. 1 is a schematic drawing depicting the components and communicative connections of an exemplary IVUS system suitable for integration with catheter lab/operating room infrastructure.

Turning to FIG. 1, a photographic image depicts a set of the primary components of an IVUS system suitable for integration in a catheter lab/operating room environment. It is noted that the exemplary installation depicted in FIG. 1 depicts mounting/placement of the various components on a "shortened" patient table 102 (used for demonstration purposes). In an actual operating room environment the table is significantly longer and more sturdy in construction to support a patient during a catheterization procedure.

A processing unit 100, incorporating many of the capabilities and functionality of known personal computers, coordinates operation of the peripheral components of the exemplary IVUS system, processes commands from attached controllers, issues control commands to an IVUS device (via a PIM) and processes IVUS data received from the IVUS device to render corresponding graphical IVUS image data. The resulting IVUS image data drives communicatively coupled graphical displays. The image data is also stored on both local and networked data storage devices.

In an exemplary embodiment, a housing for the processing unit 100 has suitable dimensions to facilitate placement of the processing unit 100 in a variety of desirable locations, both proximate (e.g., on a shelf 104) and remote from the patient table. In the illustrative example the housing of the processing unit 100 occupies a space of about 16 inches square and about 6 inches deep. The dimensions of the processing unit 100 (housing) vary in accordance with various embodiments of the invention and should not be taken as limiting the scope of the invention. Furthermore, the location of the processing unit 100 is very flexible in view of its size and the signal transmission capabilities of physical communications links between the processing unit 100 and peripherally connected components including: a control panel 110, a monitor 112, and a patient interface module (PIM) 114. The interconnect cabling and the peripheral components are described further herein below.

The processing unit 100 includes a commercially available mother board with, for example, an INTEL PENTIUM Sossaman (dual-core, low-power consumption) microprocessor, 2 GB of system RAM, one 3.5" hard drive, a medical grade power supply, an ultrasound signal processing card, and a remote control interface card. In an exemplary embodiment the external interface of the processing unit 100 and embedded control logic support multiple, simultaneously active (i.e., sending asynchronously processed control instructions to the processing unit 100) control panels (e.g., control panel 110) and multiple remote monitors (e.g., monitor 112). The multiple control panels and remote monitors are not limited to two, and can indeed exceed two. Support of multiple active controllers (e.g., control panel 110) allows two or more users to send control signals governing the operation of the system to the processing unit 100 without locking out any of the simultaneous users. Such operating mode supports remote assistance for a user operating the local control panel 110.

The control panel 110 and the monitor 112 are connected via communications cabling supporting remote positioning/operation of the peripheral components from the processing unit 110 during a catheterization procedure. By design, the processing unit 100 is compact, relatively light weight, very quiet and operates without direct user contact once powered up. The processing unit 100's housing, by way of example, incorporates mechanical mounting features (e.g., hooks, clamps, etc.) allowing the processing unit 100 to be secured to mounting rails on the patient table 102. Alternatively, the processing unit 100 is mountable on wall attached rails. In various embodiments, the processing unit 100 includes a variety of storage devices including, for example: a hard drive, DVD/CD burner/player, VCR recorder/player, etc.). The secondary storage device can also be a peripheral device attached via, for example, a USB cable to the processing unit 100.

Figure 2:
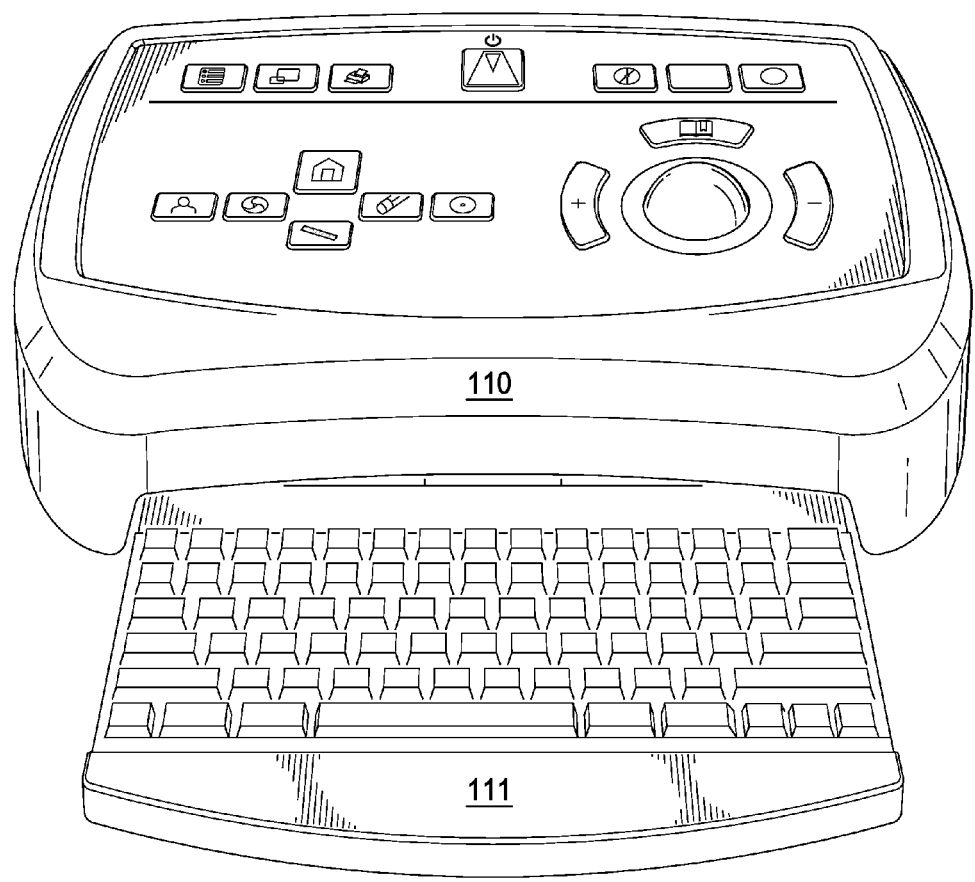
FIG. 2 depicts an exemplary control panel including a keyboard in its slideout position.

Turning to the control panel 110 component of the system, in the exemplary embodiment, the control panel 110 includes a plastic housing that holds various user input interfaces. Approximate dimensions of the control panel are: 10"×16"×4" (H×W×D). By way of example, the exemplary control panel 110 includes a slide out keyboard 111 (see, FIG. 2) and a touch interface (described further herein below with reference to FIG. 5). The enclosure is mountable on a variety of structures including, for example, a support arm attached to a rail of the patient table 102 or an articulated wall mount. The control panel 110 can be placed away from the immediate vicinity of the patient table 102 such as on a table in a remote control room or mounted to a roll around (e.g., IV pole) cart. The control panel 110 is communicatively coupled to the processing unit 100 via a cable of potentially significant length. In yet other embodiments, the control panel is located on a table near a secondary local medical grade display (not shown) which receives a copy/clone of the primary image displayed on the monitor 112. The second display (e.g., a 15 inch LCD monitor) requires an additional cable from the processing unit 100. The control panel 110 includes, by way of example, an additional USB port so that it can also be connected to a printer or other suitable USB-enabled peripheral device.

Referring now to the monitor 112, in an exemplary embodiment the monitor 112 is a 19 inch LCD monitor (e.g., an InVision monitor) for providing an image, based upon image data rendered by the processing unit 100, to viewers in the vicinity of the patient table 100. In an exemplary embodiment the monitor 112 is mounted to an articulated arm attached near the "foot" end of the patient table 102. The mounting arm incorporates many degrees of motion freedom thereby enabling rotating and positioning the monitor 112 so that it is entirely under the patient table and out of the way if desired. When needed for IVUS, the monitor 112 is repositioned so that it is easily viewed by a catheter lab technician standing near the patient table 102.

The remote control/display system supported by the processing unit 100 is used to allow remote control of the processing unit 110 by multiple remote control devices (e.g., the control panel 110). The system similarly supports remote display of video images from the processing unit 100 on multiple displays.

Primary system components on the processing unit 100 supporting communications between the processing unit 100 and a peripheral control/display device are a CPU integrated signal sender and a remote signal receiver. The interconnection is by means of a single CAT6 double shielded cable from the CPU to each of the 2 remote control panels and each of the 2 remote displays. Power is provided over the CAT6 cable so no remote power supply is required.

The exemplary system also includes a known PIM 114 to which appropriate IVUS catheters are communicatively coupled for an imaging session. The PIM 114 can be any of a wide variety of interface modules that interface imaging catheters to a processing unit such as processing unit 100.

Another notable feature of the illustrative embodiment is the ability of the components to be separated by potentially large distances. Through the use of high quality cabling (both USB and VGA) and sufficiently powered transmission interfaces (e.g., in-line buffer amplifiers), components of the system (including remote instances of peripheral control panels and monitors) are positioned outside the immediate vicinity of the patient table 100, such as across the room or even in a separate room up to 150 feet from the patient table, without significant signal loss. In an exemplary embodiment, the cable connecting the PIM 114 and the processing unit 100 is up to approximately 100 feet. In such circumstances the extended length is accommodated by a greater gauge wire in the connector cable as well as through adjustments for signal transmission delays.

In an exemplary embodiment wherein the processing unit 100 is mounted on a lower shelf of the patient table 102, the wiring to and from the processing unit 100 is routed to remotely located independently/flexibly located (remotely located) peripheral components, including possibly remotely located versions of the control panel 110 and the monitor 112, by cabling strung across the floor under suitable cable covers. Cabling for other peripheral components positioned in the proximity of the patient table 102, such as the catheter lab control panel 110 and the patient interface module (PIM) 114, are routed directly from the processing unit 100 to these components. In the illustrative example in FIG. 1, the monitor 112 is mounted to the patient table 102, in close proximity to the processing unit 100, and a direct VGA cable connection is provided. The remaining cable is CPU AC power which should be available from an AC outlet on or near the patient table mounting pedestal. There is no AC power required for the control panels attached to the CPU.

The cabling between the various components supports communications using a variety of protocols. By way of example, the control devices operate via USB and TCP/IP protocols. The video/analog cables utilize a VGA or analog Ethernet scheme. However, in alternative embodiments digital video signaling schemes are used. Finally, while cables are described for communicatively coupling the components, in alternative embodiments wireless technology links one or more of the inter-communicating components of the system.

The exemplary component-based system also includes an archive station 116. In the illustrative embodiment depicted in FIG. 1, data is moved from the processing unit 100 to a shared image data server running on the archive station 116. By way of example, the data is transmitted via Ethernet protocol to a DICOM workstation (the archive station 116) for storage within an appropriate directory or database, or alternatively burning the image data to DVD or other removable computer readable memory media. Data can also be moved from the processing unit 100 by means of a removable flash drive of, for example, 4 GB capacity. The flash drive is thereafter installed on another computer including a DVD burner for review or burning to a DVD. However, in yet another alternative arrangement, archival capabilities are provided in the form of a desk top/tower PC workstation including a commercial monitor (e.g., a 15 inch LCD) and a DVD writer. The workstation connects to the processing unit 100, for example, by means of an Ethernet. The files stored on the hard drive of the processing unit 100 are moved to the workstation for review and archiving to a DVD without impacting the operation of the processing unit 100. In still another alternative embodiment the functionality and hardware (e.g., hard drive and CD/DVD burner) of an archive station is incorporated into the processing unit 100. A printer, such as a color dye sublimation printer, is optionally attached to the workstation to permit image printing.

Figure 3:
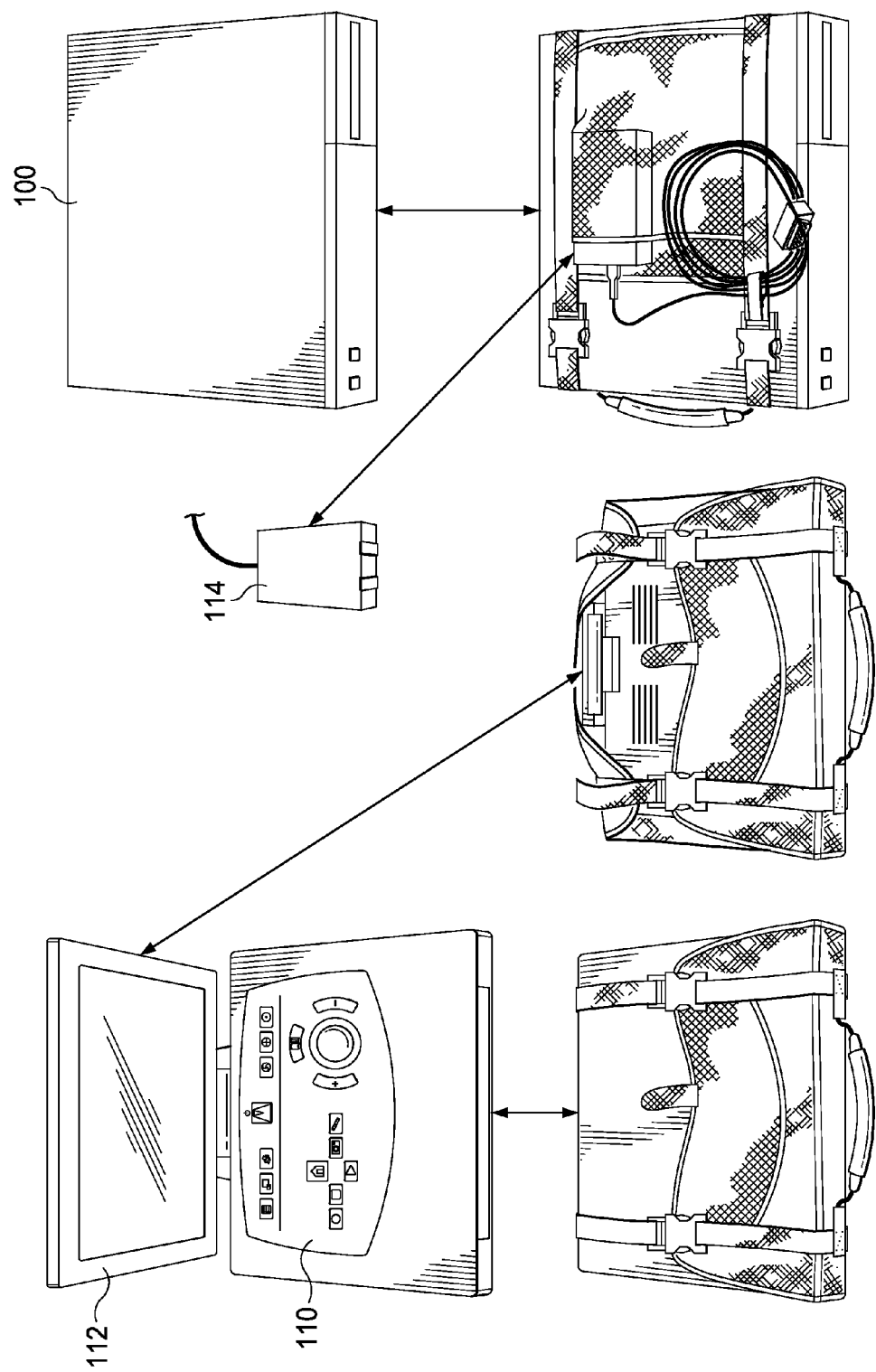
FIG. 3 depicts an exemplary portable configuration of the system including components and their associated carrying case configuration.

The componentized arrangement of the disclosed system facilitates providing a portable system. A portable version of the system (see, FIG. 3) depicted in FIG. 1 uses the same processing unit 100 depicted in FIG. 1. However, the processing unit 100 is mounted in a carrier to allow it to be easily transported. The control panel 110 and archive station 116 are transported by carriers. The monitor 112 is potentially any one of a variety of commercially available medium scale (e.g. 15 inch) LCD monitors. If desired, an optional collapsible cart, chosen from one of many commercially available models is used to transport the separately bagged/encased components.

Standard-dimensioned mounting rails are generally available in catheter labs. The installation kit for the system, by way of example, includes a set of rail mounting hardware to allow customization of the mechanical installation to meet the unique positioning requirements of each catheter lab.

Figure 4:
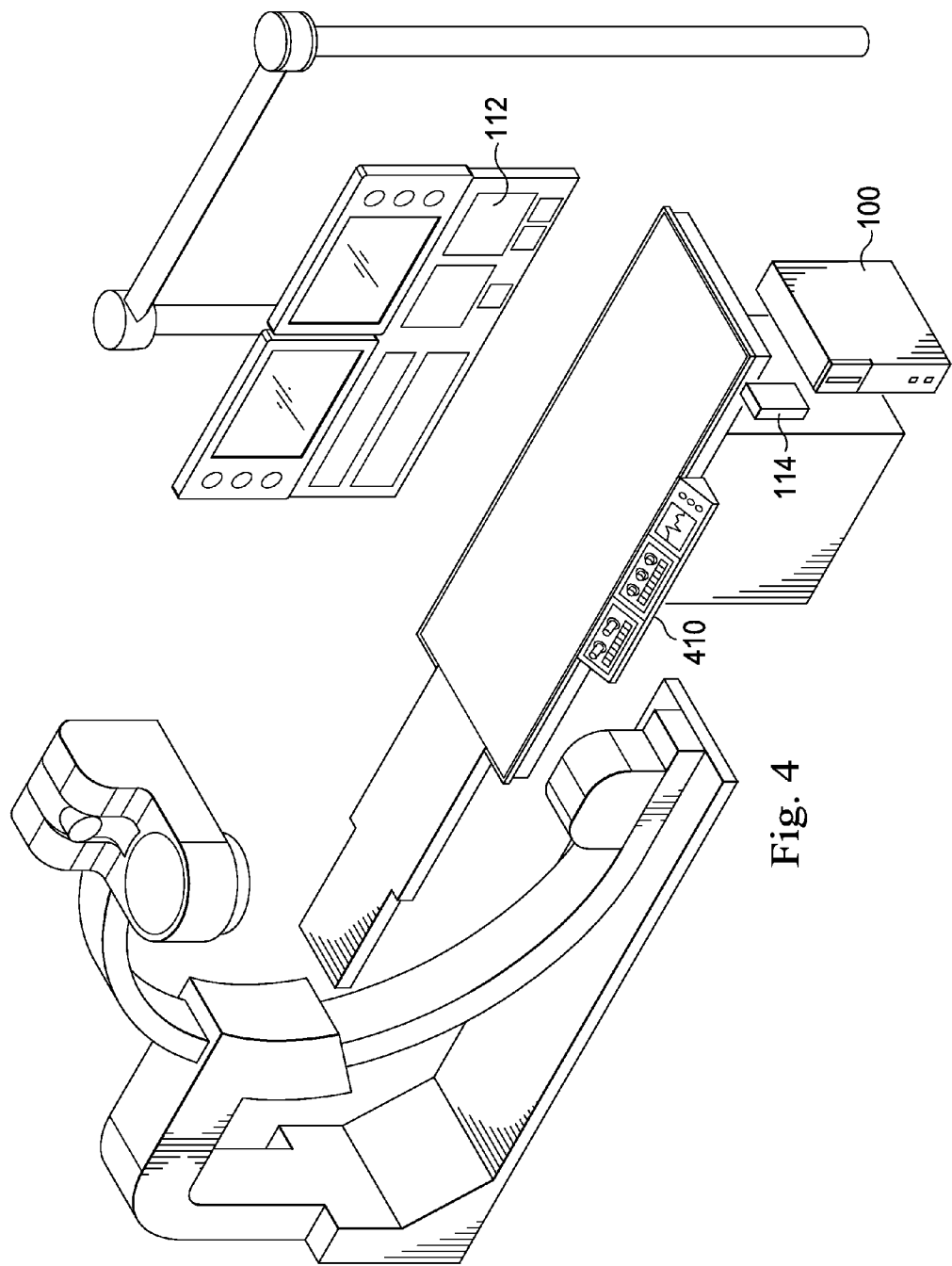
FIG. 4 depicts an exemplary integrated system including an integrated third party controller.

Another aspect of the disclosed system is interoperability support. In the exemplary embodiment, the processing unit 100 includes an Ethernet connection that allows connection of the processing unit 100 to a hospital LAN, DICOM workstation, archive workstation, or remote control consoles such as ones provided from GE (see, e.g., controller 410 in FIG. 4), Siemens or other manufacturers. In support of this functionality, one or more additional software modules are provided to interpret commands issued by these remote control devices and provide the proper response (including image data translators to match the supported protocols of the attached devices and their associated image display systems).

The following summarizes a set of functional/operational features of an exemplary componentized system described herein above. First, the system unobtrusively integrates with existing equipment in a catheter lab. As such the system can always be in position, always powered and ready to perform an IVUS imaging session. Second, the system occupies no floor space. Third, the system does not noticeably alter the lab's working environment since it generates very little noise (the low power processors generate less heat and therefore smaller fans can be used). Fourth, the system accepts, and processes control commands issued from multiple, simultaneously active distinct controllers. Multiple users can simultaneously submit control commands that are processed as they are received by the processing unit 100. Similarly, the system supports multiple, potentially remotely located, monitors for displaying IVUS images rendered by the processing unit 100. Sixth, the system can be dismantled and packaged in hand-held portable carriers in a portable embodiment. The above functionality is provided by a system that incorporates all the functional capabilities of full-size currently available IVUS systems.

While various examples are provided herein, it is noted that other embodiments include any of a variety of alterations. For example, the processing unit 100 can occupy any of a variety of form factors such as a cube. The motherboard of the processing unit 100 is, by way of example, any microATX or ATX sized board, allowing any of the commercially available PENTIUM processors to be used. The control panel 110 can be connected by means of a WiFi connection using suitable adapters. The video image from the IVUS system can be broadcast to remote locations using wireless technology. Any number of monitors, keyboards, trackballs or mice can be attached to the processing unit 100 and used simultaneously (no controller lock out) with their asynchronous requests being handled as they are received by the processing unit 100. By adding suitable interface software, the processing unit 100 can be controlled from the control panels of patient tables or X-Ray consoles made by GE, Philips, Siemens, etc.

The following summarizes features and performance characteristics of the componentized system depicted in FIG. 1, some of which have been discussed previously herein above.

Generated/Displayed Images

The system supports a combination of tomographic and sagittal views including: tomographic IVUS images, sagittal views either vertically or horizontally simultaneous with tomographic display. All measurements are displayed on imaging views. Data capture and display is carried out in the form of recorded video loops and still images. The system supports replaying and reviewing captured images, data capture and display in all modes including: Virtual Histology and blood flow imaging modes. A variety of imaging technologies include Intracardiac Echocardiography (ICE), flow, pressure, etc.

With regard to the display screen, text is displayed by default in English. Additional supported languages include: French, Italian, German, and Spanish. Other displayed information includes: patient demographic information; current date, time, software version; patient co-morbidity data (in the patient screen); measurements, including distances, areas, longitudinal distances, and borders.

Catheter Support:

The processing unit 100 supports a variety of cardiovascular and peripheral IVUS catheters (both array and rotating crystal) and flexibly supports later developed catheter designs including Intracardiac Echocardiography (ICE) and capacitive Microfabricated Ultrasonic Transducer (cMUT) catheters.

Instrument Set Up/Functions:

Standard local video output is provided as well as multiple remote video outputs. Communications set up include network (DICOM) and ETHERNET RJ-45. A connector on the processing unit 100 chassis supports remote USB control panel, trackball or keyboard input. The system supports communication with a remote archiving station for color image printing and DVD recording of patient data. The system supports interfacing with controls of others including GE, Siemens, Philips, etc.

Mechanical Design:

The system components all have computer components and printed circuit boards integrated into a small, reduced weight, housing, suitable for mounting on, or near the patient table in a catheter lab or alternatively a remote location within 30-50 meters of the patient (depending on the component) in a remote control or equipment room. The control panel 110 is mounted from the DIN rails on the patient table 102 in the catheter lab and/or a remote control room. The control panel 110 connects to the processing unit 100 by a single cable. The control panel 110 also includes mounting hardware for mounting from a roll around equipment cart or from a wall. The Control Panel enclosure is also attachable to a boom/arm/mount that can be mounted on or to the control area of the patient table. It should also be capable of being mounted to a roll around IV pole cart. It should also be possible to place it on a flat table for desktop use.

Display:

The monitor 112 is any of a variety of available monitors including 15/17/19 inch (diagonal) flat panel LCD monitors. The monitor is of suitable quality such that the monitor screen is visible in a reduced light catheter lab environment with minimal distortion when viewed from side or off angle (up to 40-45 degrees off angle). The display is mountable in a variety of ways including on an articulated arm that allows the display position to be changed from stowed under the patient table, to easily visible at the patient table. The display is also mountable via a bracket attached to the patient table 102.

Control Panel:

The control panel connects to the processing unit 100 via a USB cable and permits operation of the GUI and patient data entry using the pull out keyboard. The control panel is mountable on or near the patient table 102, on a freestanding mobile IV pole carrier, or from an articulated wall mounted arm, depending on user preferences. The control panel communicates with the processing unit from a remote control room User Interface:

The user interface embodied in the monitor 112 displays and the control panel 110 (described herein below) provide an intuitive, easy to use interface that follows a typical IVUS case workflow. The user can use the mechanical buttons/keys on the control panel or, after powering on, navigate via soft button controls on the user interface. The primary operator control is provided through on-screen curser and screen controls on the monitor 112 display. When operating in a mode where Virtual Histology functionality is active, the system supports plaque/tissue characterization and volume determinations, including user-driven border editing on the tomographic and in-line digital views, and reanalysis of statistics. A remote archiving station consolidates the tasks of saving data, printing data and/or networking data.

Data Storage:

A variety of data storage is supported by the exemplary system including the following:

Primary Storage Medium: Internal CPU hard drive(s).

Secondary Storage: Media will be DVD-R disks for archival purposes.

Tertiary Storage: Hospital DICOM server via the PACS network.

Quaternary Storage: Removable USB flash drive for transfer to a workstation.

Ability to review data on systems from both primary and secondary sources.

Ability to view Volcano images on a computer, such as in their office or home Minimum three, 90 second video loops stored @ 30 fps LCD/CPU Specification In an alternative embodiment the monitor 112 and the processing unit 100 are contained within a single housing and used in hospital catheter laboratories. It is designed to mount from the patient table mounting rails using mounting hardware. The following specifications describe the design details for this variation of the above-described componentized system.

The case has overall dimensions of 15" H×17" W×5" D and a weight of approximately 25 pounds (about 10 Kg). Cooling is provided via a 1×80-120 ccm cooling fan, blowing air into case, exiting from bottom or sides. The processor is a low power, dual-core PENTIUM Sossaman processor.

The motherboard includes at least two PCI slots for connecting hosted digital and analog boards of the processing unit 100.

Figure 5:
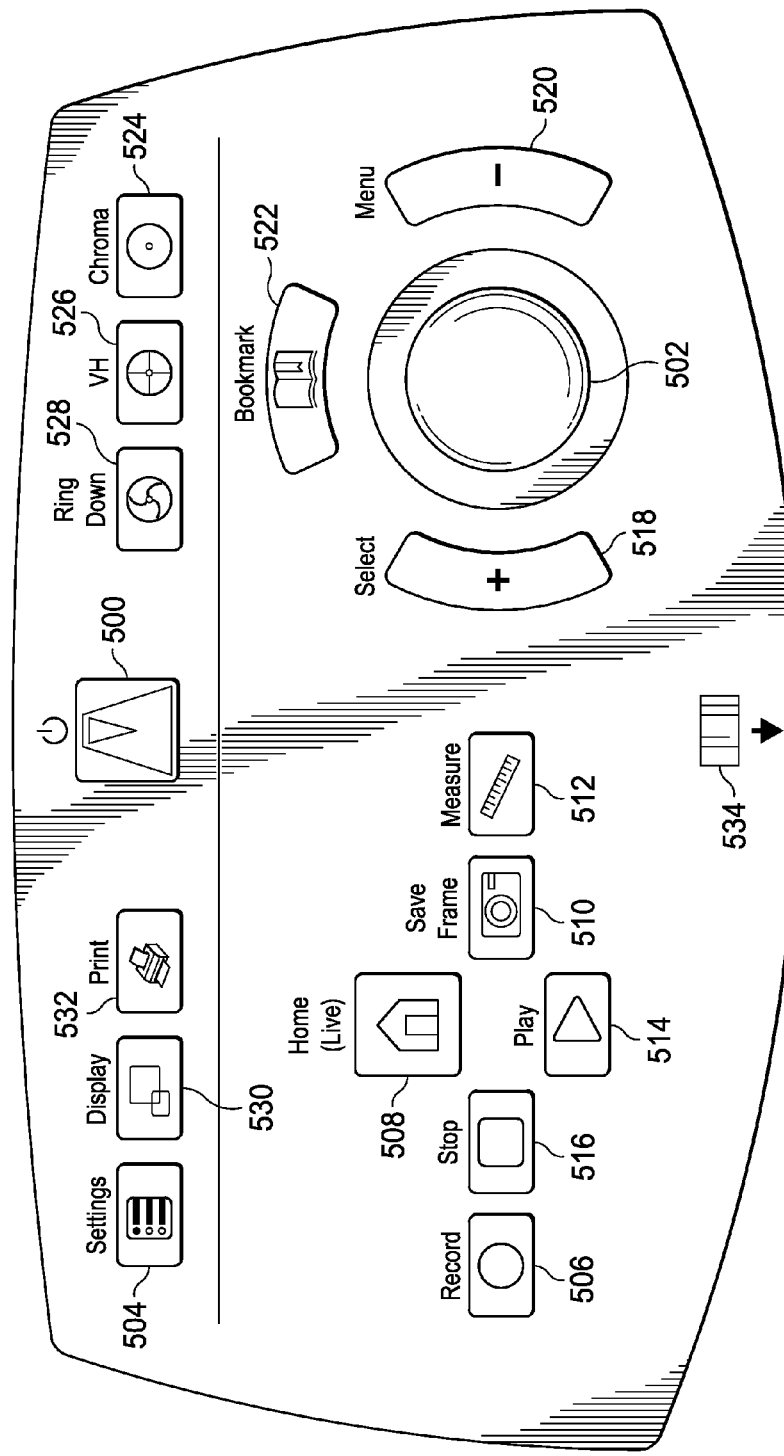
FIG. 5 illustratively depicts an exemplary control panel configuration including a trackball pointer control.

Turning to FIG. 5, an exemplary control panel button/trackball interface is depicted. In general, a user interacts with the system through the control panel 110 via a set of buttons configured, by way of example in a manner set forth in FIG. 5. The elements of the control panel include: a Power on/off

500; a trackball 502 (used to position the cursor on the screen of the monitor 112); screen selection buttons including settings 504, record 506, home 508, save frame 510, measure 512, play 514, and stop 516; select + 518 and menu − 520 buttons; a bookmark button 522; a standard alphanumeric keyboard (retracted below control panel); a Chroma button 524 (for activating the CHROMAFLO flow imaging feature); a VH button 526; a ringdown button 528; a display button 530; a print button 532; and a keyboard indicator 534. The functionality of each of these elements is discussed herein below.

In an exemplary embodiment the various action/control buttons are grouped to facilitate user workflow and include color-coded coordination with software buttons and icons to promote ease of use. The power button 500 turns the system on or off and illuminates when the system is plugged in. In addition to the power button 500, a set of buttons (e.g., settings 504, display 530, and print 532) along a top row of the control panel facilitates system set-up and mode selection. These top-row buttons/actions are generally not part of the routine work flow. The two groups include:

Set-Up & Display

The settings button 504, when selected, changes system settings such as date and time; the settings button 504 also permits setting and editing default configurations.

The display button 530, when selected, displays a large IVUS image with measurements and demographics to facilitate large viewing.

The print button 532, when selected, prints a 6×4 inch photo of the current image on the screen.

Modes

The ringdown button 528 is selected to turn the ringdown functionality of the system on or off.

The VH Mode button 526, when selected by a user, initiates turning the Virtual Histology (VH) display on or off.

The Chroma button 524, when selected, turns the CHROMAFLO flow imaging feature on or off.

Two groups of buttons/controls lie below the top row. The two groups are action-oriented and designed with the user in mind to facilitate ease of use and retention of training. These buttons are typically used during a routine patient case:

Workflow Buttons that Facilitate Ease of Use of System

The record button 506 is selected to record a video loop.

The stop button 516, when pressed by a user, stops the recording of a video loop. Pressing the stop button 516 while viewing a live image freezes the live image.

The home button 508, when pressed, presents the live image for viewing.

The play button 514 is selected to play a recorded video loop.

The save frame button 510 is pressed during a live image display mode to save one frame of live image data.

The measure button 512, when selected, provides access to measurement options such as diameter, length and borders.

Buttons Grouped Around the Trackball to Facilitate Navigation During the Patient Case The select + button 518 is pressed to select tabs, areas, or points. The select + button 518 is similar in functionality to a left-click button on a mouse.

The menu − button 520 is pressed to end selection points. The menu − button 520 is similar in functionality to a right-click button on a mouse.

The bookmark button 522 is pressed while recording a loop to select specific areas of interest.

Trackball 502

The trackball 502 moves the cursor on the monitor 112 to allow function selection. The trackball 502 is also useful for selecting annotation locations and making measurements.

The keyboard symbol 534 points to the retractable keyboard beneath the control panel top shell.

Alphanumeric Keyboard

A standard alphanumeric keyboard is contained in a retracting tray under the control panel button/user interface and is used for data entry and image annotation. To use the keyboard, a user pulls a latch underneath a keyboard tray and pulls the keyboard tray out.

Figure 6:
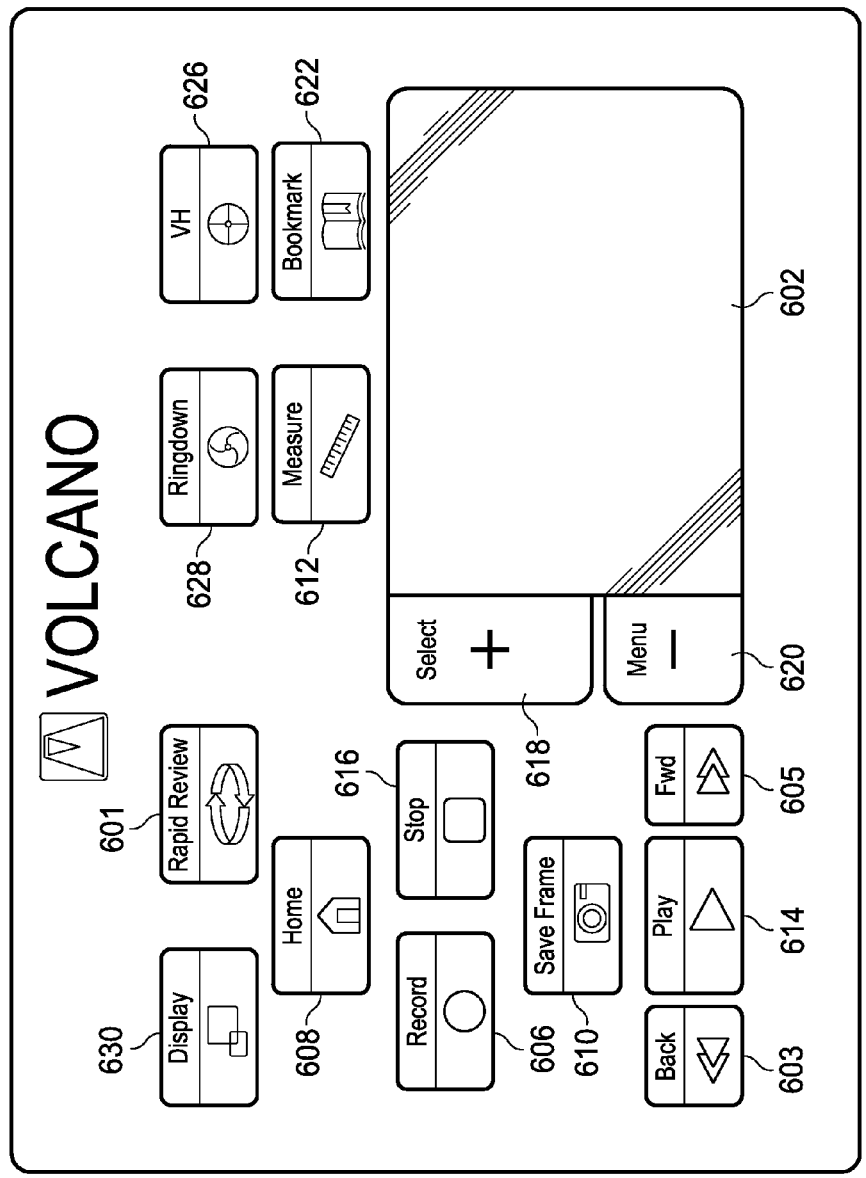
FIG. 6 illustratively depicts an exemplary control panel configuration including a touchpad pointer control.

Turning to FIG. 6, an illustratively depicted touchpad controller offers most of the functionality of the controller described hereinabove with reference to FIG. 5 with the exception of a keyboard and settings, print, and Chroma buttons. The controller is a compact sealed unit adapted for use alongside a patient table. A quick-action mount (see, e.g., FIGS. 9*a* and 9*b*) provides easy table mounting and removal. The touchpad controller depicted in FIG. 6 is connected to the workstation computer via a standard I/O cable (e.g., USB). In addition, the controller depicted in FIG. 6 provides rapid review 601, back 603 and forward 605 buttons supporting: rapid review (cycling though a selected frame sequence), back (one frame), and forward (one frame) display controls. Holding down the back 603 or forward button 605 causes the system to repeatedly scroll through an entire multi-frame loop until the button 603 or 605 is released by a user. The IVUS system supports receiving input from multiple active controllers. Thus, in an illustrative embodiment, a first user potentially uses the controller depicted in FIG. 5 while another user operates the controller depicted in FIG. 6.

In general, a user interacts with the system through the controller depicted in FIG. 6 via a touchpad and a set of buttons configured, by way of example in a manner set forth in FIG. 6. The elements of the control panel include: a touchpad 602 (to position the cursor on the screen of the monitor 112); screen selection buttons including: record 606, home 608, save frame 610, measure 612, play 614, and stop 616; select + 618 and menu − 620 buttons; a bookmark button 622; a VH button 626; a ringdown button 628; and a display button 630. The functionality of the controller user interface elements is discussed herein below.

In an exemplary embodiment the various action/control buttons (alternatively referred to as keys) are grouped to facilitate user workflow and include raised rims and color-coded coordination with the software button controls and icons to promote ease of use. A set of buttons along a left side of the top row (e.g., display 630, and rapid review 601) facilitate operating mode selection.

Display and Rapid Review:

The display button 630, when selected, toggles displaying a large IVUS image with measurements and demographics to facilitate large image viewing.

The rapid review button 601, when selected, initiates displaying a continuous loop of selected image frames based upon a selected frame of interest and a previously chosen number of frames the user wishes to review before and after the frame of interest, along with a rate at which to view the entire chosen loop.

The ringdown button 628 is selected by a user to toggle the ring down functionality of the IVUS system between on and off.

The VH Mode button 626, when selected, toggles the Virtual Histology display between on and off.

Buttons/controls lying below the top row are generally action-oriented and designed with the user in mind to facilitate ease of use and retention of training. These buttons are typically used during a routine patient case.

Workflow Buttons that Facilitate Ease of Use of System

The record button 606 is selected by a user to commence recording a video loop (or stream) comprising a sequence of IVUS image frames.

The stop button 616, when selected, stops the recording of a video loop. Pressing the stop button 616 freezes a live image. The IVUS system continues to acquire and process image frames. However, they are not recorded on the video loop/steam.

The home button 608, when pressed, causes the system to display for viewing the current live image.

The play button 614 controls playing a recorded video loop/stream. Selecting the play button 614, by way of example, toggles between playing and pausing the display of the currently playing video loop/stream.

The back button 603 enables a user to step back a single frame at a time from a currently displayed frame in a paused play sequence. Holding down the back 603 button allows the user to scroll continuously through all of the images that comprise the video loop until the function button is released.

The forward button 605 enables a user to step forward a single frame at a time from a currently displayed frame. Holding down the forward 605 button allows the user to scroll continuously through all of the images that comprise the video loop until the function button is released.

The save frame button 610 enables a user to select the save frame button 610 during Live mode (entered by selecting the home button 608) to save one frame.

The measure button 612, when selected provides access to measurement options such as diameter, length and borders.

Buttons Grouped Around the Touchpad 602 to Facilitate Navigation During the Patient Case The select + button 618 is pressed to select tabs, areas, or points. It is similar to left-clicking with a mouse.

The menu − button 620 is pressed to end your selection points. It is similar to right-clicking with a mouse.

The bookmark button 622 is pressed while recording a loop to select specific areas (image frames) of interest.

In an illustrative embodiment, the touchpad 602 comprises a sensor array printed circuit board that senses touch (e.g., pressure) on sequences of array elements and moves the cursor on the monitor 112 accordingly to allow selection of supported functions. The touchpad 602 is also useful for selecting annotation locations and making measurements. The touchpad 602 enables a user to manipulate the cursor position through a sterile drape with gloves on. Fine cursor/pointer movements are supported, improving operation of functions such as making measurements.

The touchpad controller is double-insulated, thereby allowing the device to be mounted alongside a patient without requiring additional grounding cables. Furthermore, raised rims/edges outline the buttons and touchpad to facilitate providing tactile feedback regarding the location of a user's fingertips within the controller user interface.

Figure 7A:
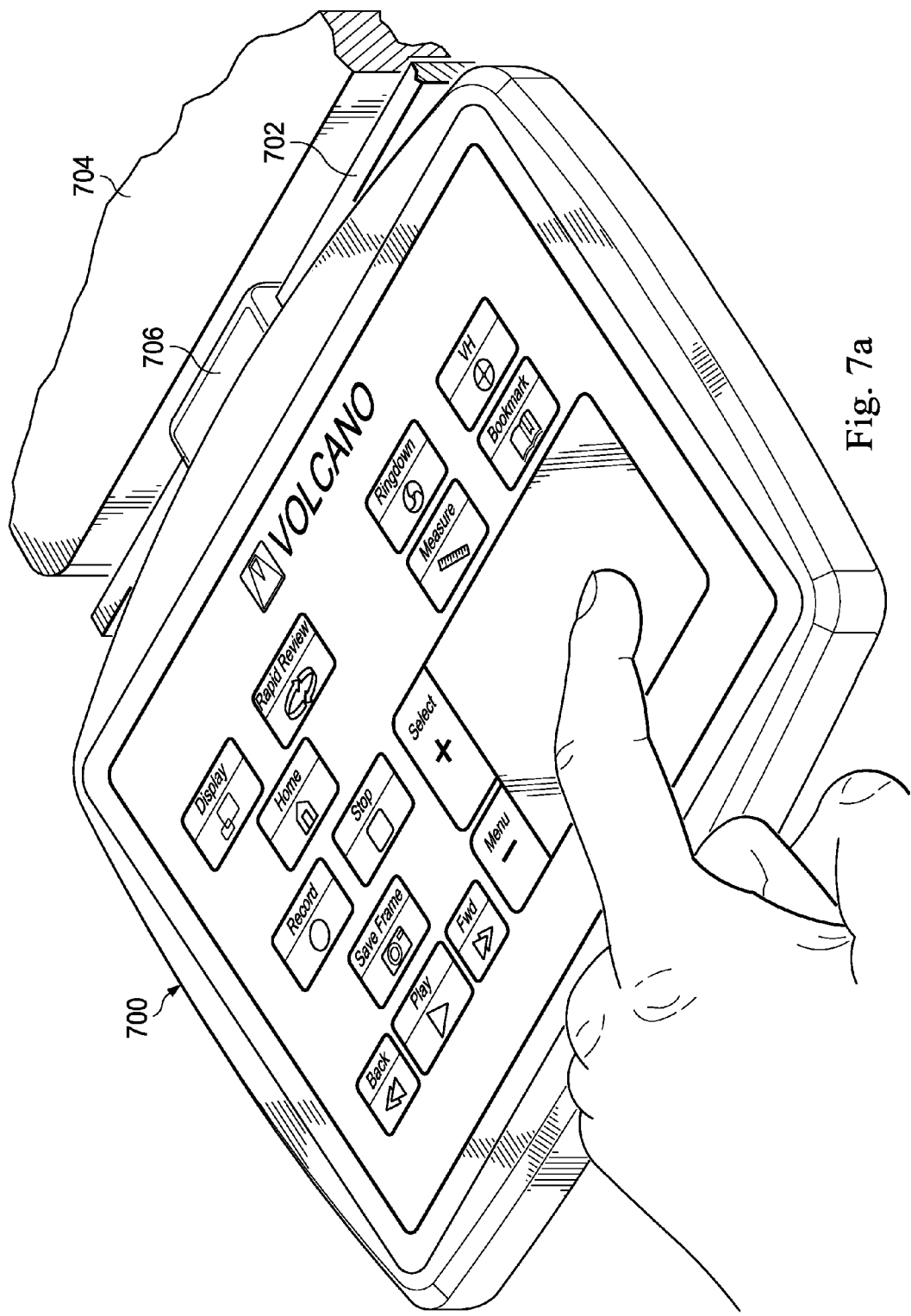
FIG. 7a is a photograph of an exemplary first arrangement for the touchpad control panel wherein the control panel is mounted on a rail running along a patient table.

Turning briefly to FIG. 7a, a photographic image is provided of an exemplary first arrangement for the touchpad control panel. In the first arrangement, the control panel 700 is mounted on a rail 702 running along a patient table 704. A mounting bracket 706, or other suitable mounting mechanism, facilitates fast and easy attachment of the control panel 700 to the side of the patient table 704. The housing of the control panel 700 is fabricated, for example, from cast urethane.

Figure 7B:
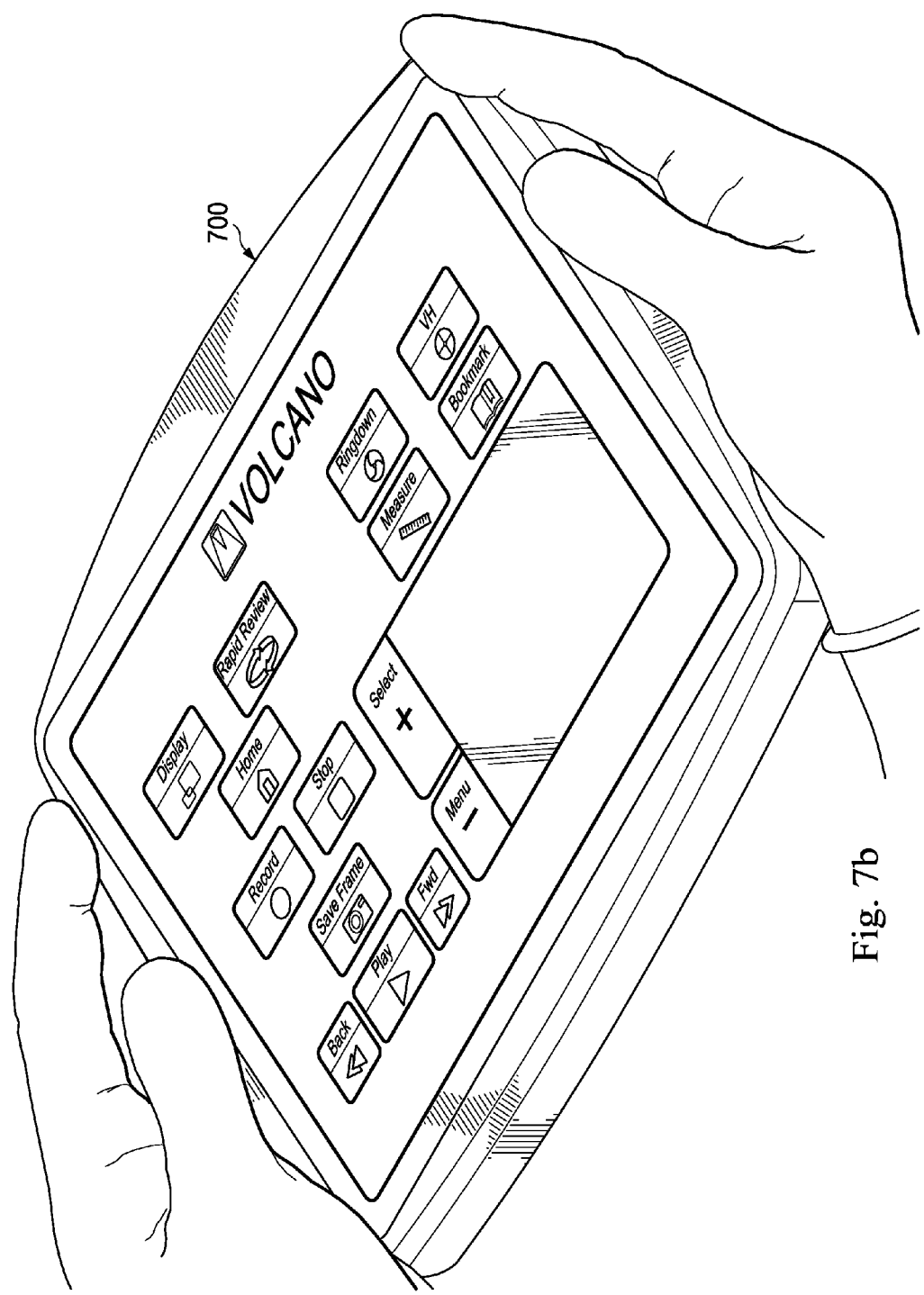
FIG. 7b is a photograph of an exemplary second arrangement for the touchpad control panel wherein the control panel is held in (gloved) hands of a user.

FIG. 7b is a photograph depicting an exemplary second arrangement of the touchpad control panel. In the second arrangement, the control panel is held in (gloved) hands of a user. The handheld feature of the touchpad control panel is facilitated by the relatively light weight (e.g., about one kilogram −34 ounces, or less) and the sizing of the control panel in relation to the size of a typical user's hands.

Figure 7C:
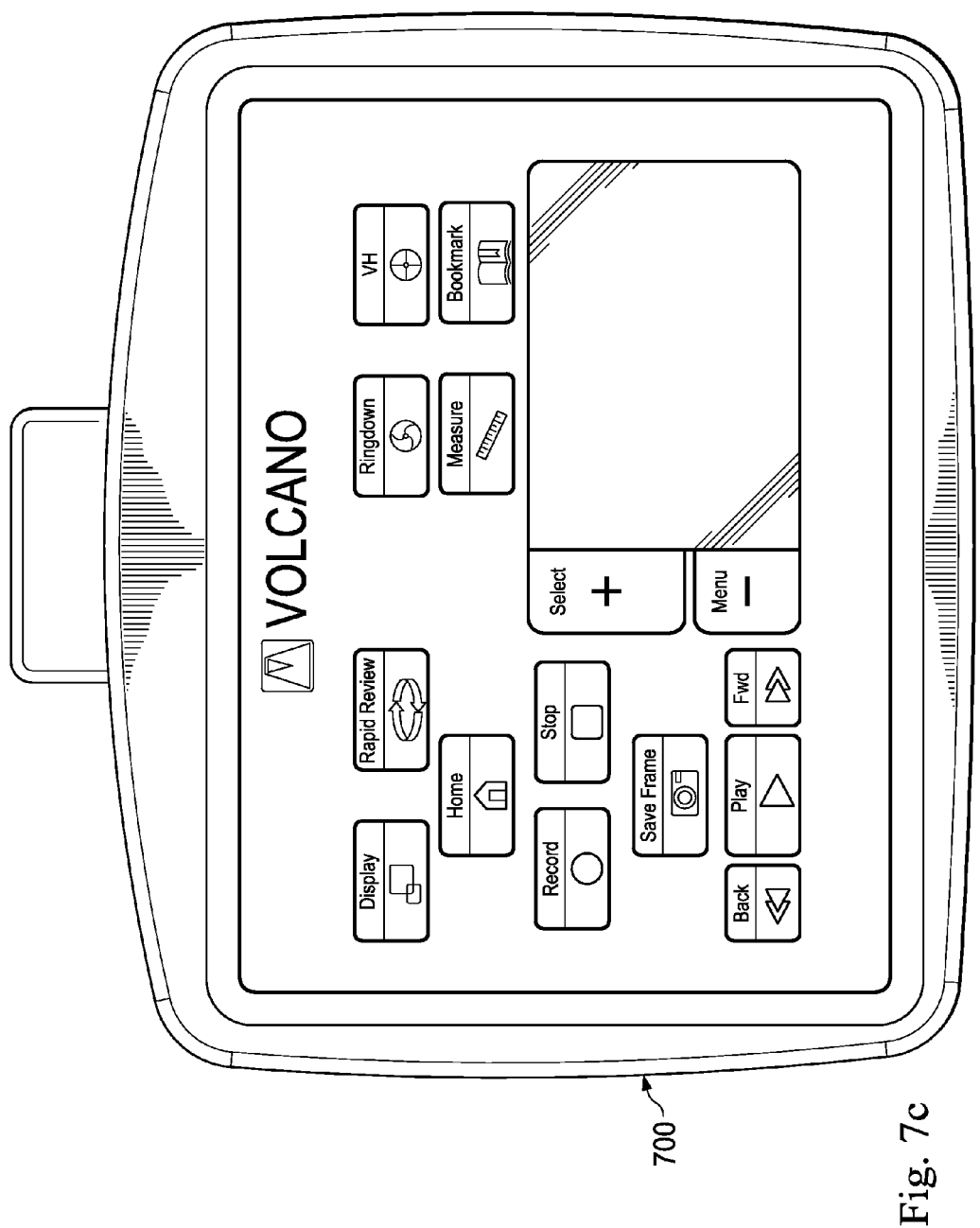
FIG. 7c is a drawing schematically depicting the control panel face and including exemplary dimensions for the handheld control panel device.

The dimensions of an exemplary top face of the touchpad control panel are provided in FIG. 7c. In the exemplary embodiment, the height of the front face is about 7 inches and the width is about 8 inches. The dimensions vary in accordance with alternative embodiments. In general, the dimensions are less than about 10 inches by 10 inches, but are sufficiently large (e.g., not less than 4 inches by 6 inches) to facilitate easy selection of the limited set of control buttons and to move a graphical pointer using the pointer control area of the touchpad controller.

Figure 7D:
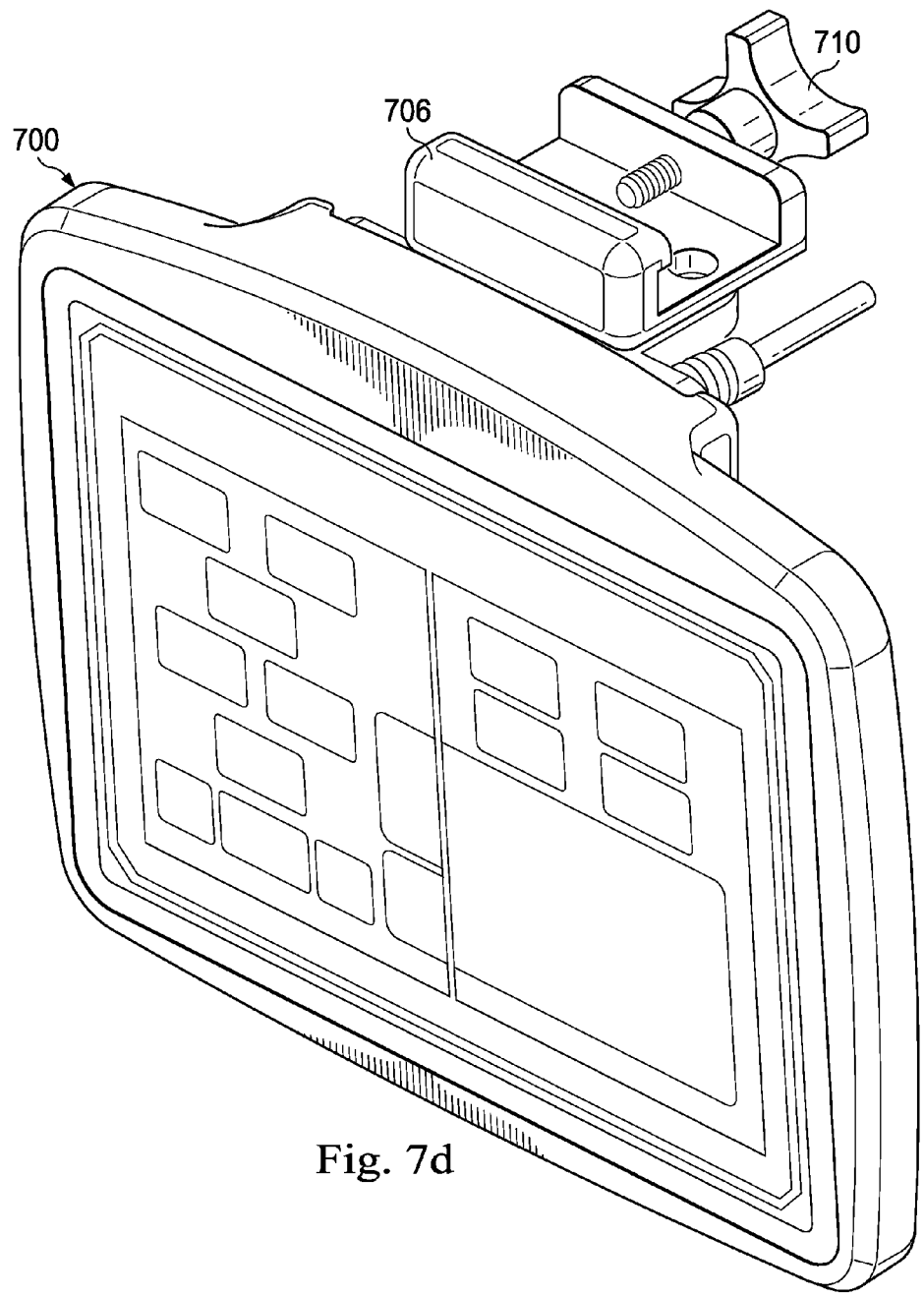
FIG. 7d is an isometric perspective view of the exemplary touchpad control panel with a front sheet removed to reveal a touchpad pc board with regions outlined for the various buttons and the touchpad pointer control.

FIG. 7d provides an isometric perspective view of the exemplary touchpad control panel with the front sheet (identifying the location of various buttons) removed to reveal a touchpad printed circuit board with regions of the sensor array outlined for the various buttons and the touchpad pointer control. The exemplary touchpad array is pressure sensitive, but could alternatively be temperature sensitive (or a combination of temperature and pressure sensitivity). An exemplary mounting bracket 706 (aluminum) depicted in FIG. 7d includes a screw clamp 710 comprising machined aluminum.

A side view of the touchpad control panel 700 is provided in FIGS. 8a and 8b. The panel 700 is connected to a control computer via a cable 712 (e.g., a USB cable) that contains both power and communications capabilities. The side view of the exemplary control panel depicts an exemplary relationship between the control panel 700 and the mounting bracket 706 including the screw clamp 710 for mounting the control panel to a patient table rail. Also, the side view shows that the control panel 700's main body (excluding the mounting bracket) is less than about two inches. More particularly, the control panel 700's body tapers from a thickness of about 1.4 inches to 0.7 inches.

Figure 9A:
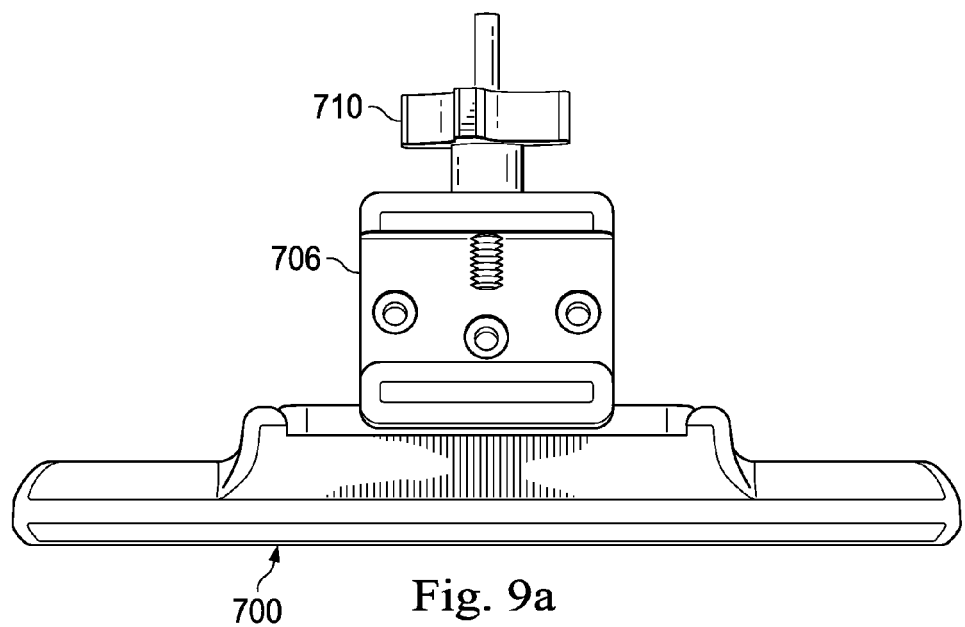
FIGS. 9a and 9b depict side views of the touchpad control panel including a mounting bracket for attachment to a rail of a patient table.
Figure 9B:
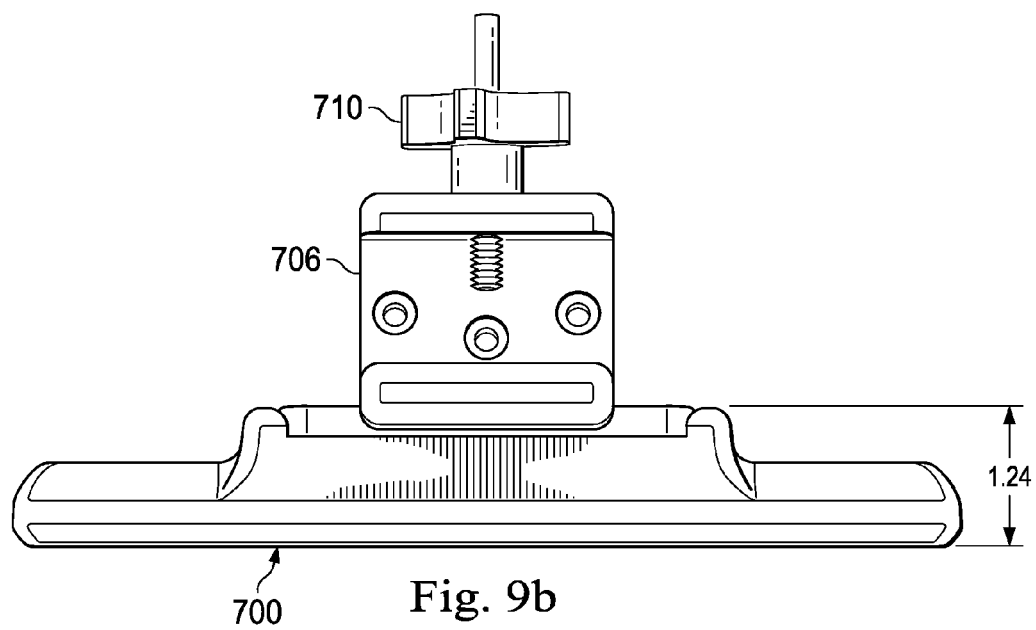

Turning now to FIGS. 9a and 9b, additional side views are depicted of the touchpad control panel 700. The mounting bracket 706 and screw clamp 710 are also depicted from a perspective of the patient table to which the control panel 700 is potentially attached via the mounting bracket 706.

Systems and their associated components have been described herein above with reference to exemplary embodiments of the invention including their structures and techniques. In view of the many possible embodiments to which the principles of this invention may be applied, it should be recognized that the embodiments described herein with respect to the drawing figures are meant to be illustrative only and should not be taken as limiting the scope of invention. Therefore, the invention as described herein contemplates all such embodiments as may come within the scope of the following claims and equivalents thereof.

What is claimed is:

1. A multi-region control panel, for an intravascular ultrasound (IVUS) system, through which a user controls acquisition and display of IVUS image information, the control panel comprising:

a housing having a height between about 4 inches and about 10 inches, a width between about 6 inches and about 10 inches, and a thickness less than about 2 inches such that the control panel is sized and shaped for both handheld use and mounting on a rail adjacent a patient table, wherein the control panel includes a plurality of actuation controls grouped into regions based on functionality, wherein the regions include a first region including a set of IVUS action controls for controlling patient image data acquisition, a second region including pointer navigation controls, wherein the pointer navigation controls comprise a touch-sensitive touchpad sensor array configured to sense a touch of a user to allow the user to control positioning and actuation of a cursor on a user interface display associated with a processing unit the control panel is in communication with, the processing unit being housed separately from the control panel such that the control panel is independently positionable with respect to the processing unit, and a third region including controls for reviewing the acquired patient image data, the third region including a measure button that provides user access to a plurality of selectable measurement options;

wherein the touchpad sensor array is further configured to accept measurement inputs to make measurements on the acquired patient image data based on a selected measurement option of the plurality of selectable measurement options.

2. The multi-region control panel of claim 1 wherein the touchpad sensor array is operable when covered by a sterile drape.

3. The multi-region control panel of claim 1 wherein the touchpad sensor array is pressure-sensitive.

4. The multi-region control panel of claim 1 wherein the touchpad sensor array supports gloved touch.

5. The multi-region control panel of claim 1 wherein the pointer navigation controls support multi-button mouse functionality.

6. The multi-region control panel of claim 1, wherein the third region includes a rapid review control for viewing a pre-selected image frame sequence.

7. The multi-region control panel of claim 1, wherein the third region includes a back and a forward button set facilitating stepping through image frames a single frame at a time.

8. The multi-region control panel of claim 7 wherein the back and forward button set facilitates scrolling rapidly through multiple image frames by holding down either one of the forward button or back button.

9. The multi-region control panel of claim 1 further comprising a mounting bracket for mounting to a rail of a patient table.

10. The multi-region control panel of claim 9 wherein the mounting bracket comprises a screw clamp.

11. The multi-region control panel of claim 1 having a weight of about one kilogram or less.

12. The multi-region control panel of claim 1, wherein the plurality of selectable measurement options includes at least one of a diameter measurement option, a length measurement option, and a border measurement option.

13. The multi-region control panel of claim 1, wherein the plurality of selectable measurement options includes a diameter measurement option, a length measurement option, and a border measurement option.

14. An intravascular diagnostic system, comprising:
an intravascular device;
a processing unit configured to issue control commands to the intravascular device and process data obtained by the intravascular device; and
a control panel communicatively coupled to the processing unit, the control panel being housed separately from the processing unit, wherein the control panel has a height between about 4 inches and about 10 inches, a width between about 6 inches and about 10 inches, a thickness less than about 2 inches, and a weight less than about one kilogram such that the control panel is sized and shaped for both handheld use and mounting on a rail adjacent a patient table, wherein the control panel includes a plurality of buttons and a touchpad, the plurality of buttons arranged to facilitate user control of the intravascular device, wherein the plurality of buttons are grouped based on functionality, a first group of the plurality of buttons is associated with operating mode selection, a second group of the plurality of buttons associated with actions of the intravascular device, and a third group of the plurality of buttons associated with reviewing the data obtained by the intravascular device, the third group including a measure button that provides user access to a plurality of selectable measurement options, wherein the touchpad is configured to sense a touch of a user to allow the user to control positioning and actuation of a cursor on a user interface display associated with the processing unit, and wherein the touchpad is further configured to accept measurement inputs to make measurements on the data obtained by the intravascular device based on a selected measurement option of the plurality of selectable measurement options, and wherein the control commands issued to the intravascular device by the processing unit are at least partially based upon user inputs made via the control panel.

15. The intravascular diagnostic system of claim 14, wherein the control panel is communicatively coupled to the processing unit via a single cable that provides for both power and data transmission between the control panel and the processing unit.

16. The intravascular diagnostic system of claim 14, wherein the control panel is communicatively coupled to the processing unit via a wireless connection.

17. The intravascular diagnostic system of claim 16, wherein the wireless connection is a WiFi connection.

18. The intravascular diagnostic system of claim 14, wherein the plurality of buttons of the control panel are color-coordinated with software generated button controls of the user interface display.

19. The intravascular diagnostic system of claim 14, wherein the touchpad is temperature sensitive to sense the touch of a user.

20. The intravascular diagnostic system of claim 14, wherein the touchpad is pressure sensitive to sense the touch of a user.

21. The intravascular diagnostic system of claim 14, wherein the touchpad is pressure sensitive and temperature sensitive to sense the touch of a user.

22. The intravascular diagnostic system of claim 14, wherein the control panel is sealed and double insulated to facilitate use alongside a patient without requiring a grounding cable.

23. The intravascular diagnostic system of claim 14, wherein the plurality of selectable measurement options includes at least one of a diameter measurement option, a length measurement option, and a border measurement option.

24. The intravascular diagnostic system of claim 14, wherein the plurality of selectable measurement options includes a diameter measurement option, a length measurement option, and a border measurement option.

* * * * *